United States Patent
Wang

(10) Patent No.: US 7,355,155 B2
(45) Date of Patent: Apr. 8, 2008

(54) LIGHT EMITTING APPARATUS FOR MEDICAL APPLICATIONS

(75) Inventor: Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 0 days.

(21) Appl. No.: 11/551,709

(22) Filed: Oct. 21, 2006

(65) Prior Publication Data

US 2007/0090272 A1    Apr. 26, 2007

Related U.S. Application Data

(60) Provisional application No. 60/596,802, filed on Oct. 21, 2005.

(51) Int. Cl.
G01J 1/04 (2006.01)
G02B 6/20 (2006.01)
A61B 1/07 (2006.01)

(52) U.S. Cl. ............... 250/205; 250/227.11; 250/552; 385/141; 362/555; 600/178; 600/182

(58) Field of Classification Search ............... 250/205, 250/227.11, 552; 385/12, 125, 141, 146; 362/555, 572, 582; 600/342, 585, 139, 178, 600/182
See application file for complete search history.

(56) References Cited

U.S. PATENT DOCUMENTS

| | | | |
|---|---|---|---|
| 5,452,395 A * | 9/1995 | Schichman et al. | 385/125 |
| 5,634,711 A | 6/1997 | Kennedy et al. | |
| 5,698,866 A | 12/1997 | Doiron et al. | |
| 6,602,275 B1 | 8/2003 | Sullivan | |
| 2005/0084229 A1 * | 4/2005 | Babbitt et al. | 385/146 |
| 2005/0270776 A1 * | 12/2005 | Allen et al. | 362/241 |

* cited by examiner

Primary Examiner—Kevin Pyo

(57) ABSTRACT

A light emitting apparatus is disclosed for medical applications including photo-dynamic-therapy (PDT), photobiostimulation (photobiomodulation), photo-sterilization, and photo-curing. The light emitting apparatus comprises a plurality of semiconductor light emitting elements, preferably light emitting diodes (LEDs) to produce a high intensity light beam, and a liquid light guide for delivering the light beam from the light source to the treatment site.

5 Claims, 1 Drawing Sheet

LIGHT EMITTING APPARATUS FOR MEDICAL APPLICATIONS

REFERENCE TO RELATED APPLICATIONS

This application claims an invention which was disclosed in Provisional Patent Application No. 60/596,802, filed Oct. 21, 2005, entitled "Light Emitting Apparatus for Medical Applications". The benefit under 35 USC §119(e) of the above mentioned United States Provisional Applications is hereby claimed, and the aforementioned application is hereby incorporated herein by reference.

FIELD OF THE INVENTION

This invention generally relates to a light emitting apparatus and more specifically to a semiconductor light emitting apparatus for medical applications.

BACKGROUND

Semiconductor light emitting apparatus, preferably light emitting diodes (LEDs), are considered to be an ideal candidate for photo-dynamic-therapy (PDT), photobiostimulation (photobiomodulation), photo-sterilization, photo-curing, and other medical applications due to their long lifetime, high wall-plug efficiency, and low heat generation.

Some examples of prior arts related to LED based medical light emitting apparatus include U.S. Pat. Nos. 5,634,711, 5,698,866, 6,602,275 and PCT patent application No. WO2005/035060. In U.S. Pat. No. 5,634,711, Kennedy et al. disclose a hand-held portable light emitting device for medical and industrial photo-curing and phototherapy applications. The hand-held light emitting device comprises an array of LEDs producing a light intensity in the range of several hundred mW/cm^2. The light beam from the LED array is delivered to the treatment site through a short fiber optic light guide mounted in front of the LED array. In U.S. Pat. No. 5,698,866, Doiron et al. disclose a phototherapeutic light comprising a low-power LED array with high packing density. The LEDs are overdriven to produce a desired light intensity of several hundred mW/cm^2. A direct illumination scheme is employed in the Doiron patent, where the LED array is placed close to the treatment site for light delivery. In U.S. Pat. No. 6,602,275, Sullivan discloses an LED panel comprising thousands of low power LEDs for therapeutic treatment of living organisms. The Sullivan patent utilizes a direct illumination scheme, where the device is intended to lie against the skin or surface, near the skin/surface, and/or from a distance ranging up to several feet from the skin/surface. In PCT patent application No. WO2005/035060, Persin et al. disclose a portable illuminator for photo-dynamic-therapy. An LED cluster is utilized to produce light in one or more desirable wavelengths. The light beam is delivered to the treatment site either through a glass or plastic light guide or through a transparent window.

The light emitting apparatus disclosed in the above-cited references produce a light intensity of <1,000 mW/cm^2 since low power LED arrays are employed, whereas in certain medical applications, a higher light intensity is desirable. The recent development of high intensity LEDs (LED arrays), especially those chip-on-board (COB) packaged LEDs (LED arrays) makes it possible to build light emitting apparatus with higher output intensity and more compact size. However, these LEDs (LED arrays) also bring the problem of increased heat generation and difficulty in light energy delivery due to their large light emitting area and beam divergence angle.

The lack of an efficient and convenient light energy delivery method is a common weakness for the previous disclosed medical light emitting apparatus. The direct illumination scheme employed in the Doiron and Sullivan patents requires the LED array to be placed close to the target object as the LED beam has a large divergence angle. This is inconvenient for some hard-to-reach areas due to the size limitation of the LED array and its supportive components (such as lenses, heat sinks, etc.). More importantly, the heat produced by the LED array will induce significant temperature increase for the treatment site in close contact. To avoid the temperature increase problem, the Kennedy and Persin patents employ glass or plastic fiber optic light guides for light energy delivery. However, the glass or plastic fiber light guides become rigid when their diameter is increased to match with the size of the LED array for efficient light energy coupling. Thus in both the Kennedy and Persin patents, the fiber optic light guide is used as a non-flexible element integrated with the LED array to form a hand-held device. This design is not suitable for high intensity LEDs (LED arrays) as the hand-held device can not provide efficient heat dissipation for the high intensity LEDs. In addition, the fiber optic light guide suffers a filling factor and hot spot issue as it is generally composed of a plurality of optical fibers bundled together where there exist both bright and dark regions when illuminated.

SUMMARY OF THE INVENTION

It is thus the goal of the present invention to provide a high intensity light emitting apparatus with efficient light energy delivery means for photo-dynamic-therapy (PDT), photobiostimulation (photobiomodulation), photo-sterilization, photo-curing, and other medical applications.

According to one aspect of the present invention, the light emitting apparatus comprises a high intensity LED (LED array) that adopts a COB package, where the LED chips are directly surface mounted on a thermal conductive substrate. The COB package allows much higher drive currents to be applied on the LED chips as well as greatly improved packing densities in comparison with traditional T-pack low power LEDs (LED arrays). As a result, the disclosed light emitting apparatus can produce a light intensity of >1,000 mW/cm^2. The light emitting apparatus is also capable to operate in a pulsed mode with peak light intensity in the range of several thousand mW/cm^2 to further enhance its treatment result. The output intensity of the light emitting apparatus can be electronically controlled to adapt for both low intensity and high intensity applications.

According to another aspect of the present invention, the light emitting apparatus comprises a flexible liquid light guide for light energy delivery. The flexible liquid light guide, formed by a plastic tube filled with transparent, high refractive index liquid, is used as a hand piece separated from the LED array. Thus the LED array can be mounted in the main console of the light emitting apparatus for improved heat dissipation. In addition, the liquid light guide features an acceptance angle three times larger than that of standard fiber light guides and a core size comparable to the surface area of the COB LED (LED array), which result in a high LED to waveguide coupling efficiency. The heat generation problem is avoided as the light source is positioned a distance away from the treatment site.

BRIEF DESCRIPTION OF THE FIGURES

The accompanying FIGURES, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
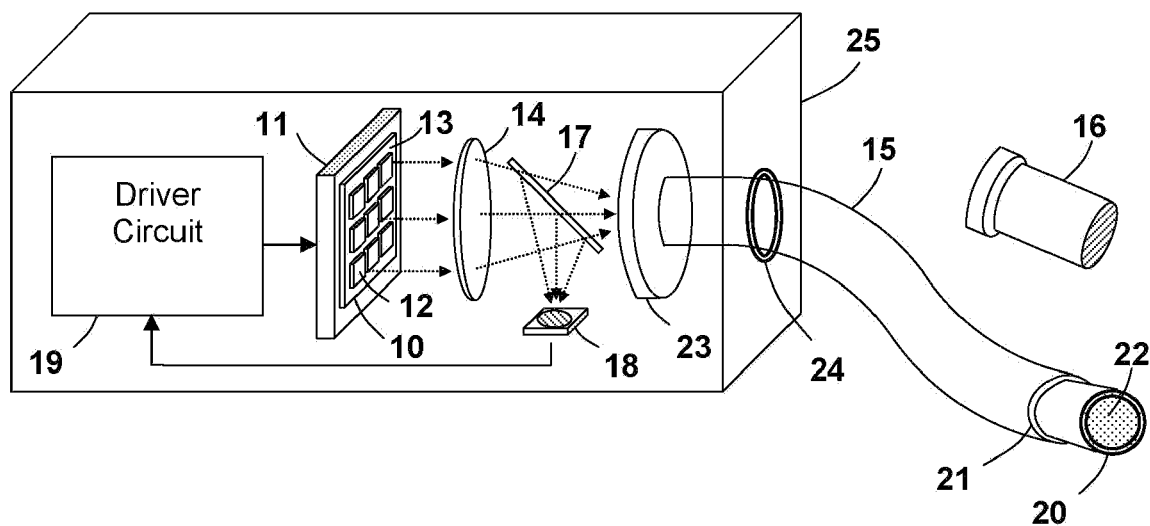
FIG. 1 illustrates a schematic structure of the light emitting apparatus.

Skilled artisans will appreciate that elements in the FIGURES are illustrated for simplicity and clarity and have not necessarily been drawn to scale. For example, the dimensions of some of the elements in the FIGURES may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a light emitting apparatus for medical applications. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

In one preferred embodiment of the present invention as illustrated in FIG. 1, the light emitting apparatus comprises a COB packaged LED array 10 mounted on a metal or ceramic heat sink 11, which may be air cooled or liquid cooled. In the COB package, the LED chips 12 are directly surface-mounted on a thermal conductive substrate 13 for improved heat dissipation. The improved heat-sinking keeps the temperature of the LED PN junction at a low level, which makes the LED capable of operating at high drive currents or output levels. The COB package allows a high packing density for the LED array so that over 85% of the total LED array surface is light emitting, which further improves the output intensity. It also leads to long lifetime as well as wavelength (color) and intensity stability. The LED chips may produce light in the ultraviolet (UV), visible, or near infrared (NIR) wavelength range depending on application requirements. The number of LED chips integrated in the array depends on the light energy requirement for a specific medical application. In this embodiment, sixteen (16) LED chips are integrated into the LED array with a total light emitting area of 3×3 mm. The light intensity produced by the LED array is >5,000 mW/cm^2. The light beam produced by the LED array 10 is focused by a set of lenses 14 and coupled into the proximal end of a flexible liquid light guide 15. The liquid light guide 15 is used as a hand piece for delivering light energy from the LED array 10 to the treatment site. Depending on the applications, a wand 16 may be attached to the distal end of the liquid light guide 15 to control the shape and divergence angle of the output light beam. A beam splitter 17 is inserted between the lens set 14 and the liquid light guide 15 to tap a small portion of the LED output and sent it to a photo detector 18 for power monitoring. The detected signal from the photo detector 18 is used to control a driver circuit 19 to regulate the drive current (thus the output power) of the LED array 10. By controlling the drive current, the output intensity of the light emitting apparatus can be adjusted to adapt for both low intensity and high intensity medical applications. By modulating the drive current of the LEDs in time domain, the LED array 10 is capable to operate in a pulsed mode. In the pulsed mode, the LEDs are switch on and off periodically with a predetermined duty cycle of <100%. Thus a higher drive current can be applied to the LED chips. As a result, the peak intensity of the produced therapeutic light can be further enhanced. The enhanced light intensity will help to improve the penetration depth of the LED light into the targeted tissue.

The liquid light guide 15 employed in the present embodiment comprises a plastic tube 20 covered by a PVC protective jacket 21. The plastic tube 20 is filled with a transparent, high refractive index fluid 22, which is used as a waveguide for light energy delivery. The tube 20 is sealed at both ends with quartz or glass windows. The core diameter of the liquid light guide 15 is selected according to the size of the LED (LED array) 10, which diameter may vary from several millimeters to a few centimeters. The liquid light guide 15 has a high numerical aperture (NA) of 0.59, which corresponds to an acceptance angle of 72°. This acceptance angle is comparable to the divergence angle of the LED light. Thus a high LED to waveguide coupling efficiency of >60% is achieved in the present embodiment. This high coupling efficiency results in a light intensity of >1,000 mW/cm^2 at the output end of the liquid light guide 15. When operating in pulsed mode, the peak output intensity can reach a level of several thousand mW/cm^2. "The flexible liquid light guide 15 can be bended over a radius of several centimeters, making it possible to illuminate those hard-to-reach areas on the treatment site." The liquid light guide 15 is fixed at the proximal end by an adaptor 23 for LED light coupling and delivers the light from the LED array to the treatment site through an output port 24. The length of the liquid light guide 15 may range from several tens of centimeters to several meters depending on application requirements. The whole light emitting module, including the LED array 10, the heat sink 11, the driver circuit 19, the feed-back beam splitter 17 and photo detector 18, the lens set 14, and the coupling adapter 23, is enclosed in a housing 25. In comparison with fiber bundle based light guides, the liquid light guide does not have the filling factor and hot spot problem. It also exhibits larger acceptance angle, larger core diameter, better transmittance in the UV and NIR wavelength regime, and a more uniform light output.

In the foregoing specification, specific embodiments of the present invention have been described. However, one of ordinary skill in the art appreciates that various modifications and changes can be made without departing from the scope of the present invention as set forth in the claims below. For example, the light emitting apparatus may also comprise vertical cavity surface emitting laser (VCSEL) diode chips. The numerical values cited in the specific embodiment are illustrative rather than limiting. Accordingly, the specification and FIGURES are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A light emitting apparatus for performing medical treatment, including but not limited to photobiostimulation (photobiomodulation), photo-dynamic-therapy (PDT), photo-sterilization, and photo-curing on a targeted site, the light emitting apparatus comprising:

an array of high power light emitting diodes (LEDs) to produce a light beam with high light intensity; and a liquid light guide having a proximal end positioned in a path of the light beam to collect and deliver the light beam to a distal end of the light guide and output the light beam to the targeted site;

wherein the liquid light guide has an acceptance angle and core diameter comparable to the divergence angle and size of the light beam to achieve a high light coupling efficiency.

2. The light emitting apparatus of claim 1, wherein the LEDs are provided in a chip-on-board (COB) package, and wherein the LEDs are directly surface mounted on a thermal conductive substrate.

3. The light emitting apparatus of claim 1, wherein the emission wavelength of the LEDs ranges from ultraviolet to near infrared.

4. The light emitting apparatus of claim 1, wherein the LEDs are operated in a pulsed mode to produce a high peak light intensity.

5. The light emitting apparatus of claim 1, further comprising a power monitor and a control unit to monitor and control the light intensity of the light beam.

* * * * *